United States Patent [19]

McLain et al.

[11] 4,432,904
[45] Feb. 21, 1984

[54] PHOSPHINE AZACROWN ETHER COMPOUNDS

[75] Inventors: Stephan J. McLain; Francis J. Waller, both of Wilmington, Del.

[73] Assignee: E. I. Du Pont de Nemours and Company, Wilmington, Del.

[21] Appl. No.: 427,357

[22] Filed: Sep. 29, 1982

[51] Int. Cl.$^3$ .............................................. C07F 9/65
[52] U.S. Cl. ................................................. 260/330.6
[58] Field of Search ..................................... 260/330.6

[56] References Cited

U.S. PATENT DOCUMENTS 3,966,766  6/1976  Lehn ................................. 260/330.6
3,997,563 12/1976  Dale et al. ........................... 549/352

FOREIGN PATENT DOCUMENTS 2086925  5/1982  United Kingdom ............. 260/330.6

*Primary Examiner*—Norma S. Milestone
*Attorney, Agent, or Firm*—James A. Costello

[57] ABSTRACT

Phosphine azacrown ethers and complexes thereof with selected cations as promoters for hydroformylation catalysts; adducts of said promoters with selected hydroformylation catalysts; process for making the promoters; and process for hydroformylation.

10 Claims, No Drawings

PHOSPHINE AZACROWN ETHER COMPOUNDS

BACKGROUND OF THE INVENTION

Powell et al., *J. Am. Chem. Soc.*, 104, (May 5, 1982) pages 2636 and 2637, describe the reaction of chlorodiphenylphosphine, an aza-thia-containing crown ether, and a tertiary amine. At page 2637 it is stated: "We are currently synthesizing metal carbonyl complexes of 2a,b and their phosphine-derivatized aza-crown ether analogues . . . ".

Tazaki et al., in *Chem. Lett.*, (1982) 571 to 574, describe the synthesis of

$CH_2(CH_2OCH_2)_nCH_2NCH_2P(O)(OH)_2$ wherein n=4,5.

The ethers and ether complexes of this invention are useful as promoters for hydroformylation catalysts. In fact, said compounds form adducts with the catalysts themselves, said adducts also being within the scope of this invention. Preferred catalysts with which the ethers and ether complexes are combined are cobalt and rhodium compounds. See Chapter 1 of "New Syntheses With Carbon Monoxide" edited by Falbe, Springe-Verlag, 1980, for a discussion of hydroformylation reactions and typical cobalt and rhodium catalysts useful therefor.

The following publications also concern Rh— and Co— containing hydroformylation catalysts: Vrieze et al., *J. Organometal. Chem.*, 14 (1968), page 185; Chatt et al., *J. Chem. Soc. A.* (1957), page 4735; and Slaugh et al., *J. Organometal. Chem.*, 13 (1968), pages 469 to 477. Typical hydroformylation reactions involving formaldehyde are discussed by Spencer, *J. Organometal. Chem.*, 194 (1980) pages 113 to 123.

SUMMARY OF THE INVENTION

This invention concerns phosphine azacrown ethers (PAC) including complexes thereof with selected cations. For convenience, the ethers and complexes of this invention can be designated $PACmn.M_{0,1}$, wherein m refers to —$CH_2$— units, n refers to —$CH_2OCH_2$— units, and M is a cation, said ethers and complexes having the formula:

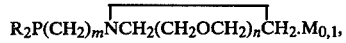
$R_2P(CH_2)_mNCH_2(CH_2OCH_2)_nCH_2.M_{0,1}$, wherein R is phenyl, naphthyl, substituted phenyl, or substituted naphthyl; m is 0 to 4; n is 3 to 6; and M is zero or one of a selected group of cations. Thus, PAC03 has the formula:

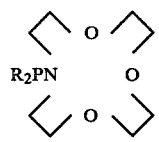

PAC14 has the formula:

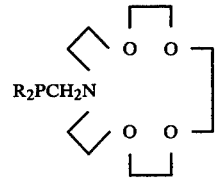

and so on.

The substituents on the phenyl and naphthyl ring(s) can be hydrocarbyl groups of up to about 6 carbon atoms (preferred); alkoxy groups of 1 to 4 carbon atoms; halogens, preferably chlorine or fluorine; primary amines; NHR' having R' of 1 to 4 carbon atoms; and $CF_3$.

There is a wide choice of cations that will form stable complexes with the ethers of this invention. Because of size considerations the choice of cation will depend somewhat on the value of n. Generally, the larger the size of the PAC, the larger the size of the cation which can be complexed therewith. Listed hereafter are a number of representative cations which can be employed with ethers of specified n values. Other combinations can be employed as will be obvious to those skilled in the art.

| n | Cation(s) |
|---|---|
| 3 | $Li^+$, |
| 4 | $Li^+$, $Na^+$, $Ca^{2+}$, $Zn^{2+}$, $Cd^{2+}$, $Hg^{2+}$, |
| 5 | $Li^+$, $Na^+$, $K^+$, $Rb^+$, $Ca^{2+}$, $Sr^{2+}$, $Ba^{2+}$, $Ra^{2+}$, $Zn^{2+}$, $Cd^{2+}$, $Hg^{2+}$, $Tl^+$, $Pb^{2+}$, (lanthanide)$^{3+}$, |
| 6 | $Li^+$, $Na^+$, $K^+$, $Rb^+$, $Cs^+$, $Fr^+$, $Ca^{2+}$, $Sr^{2+}$, $Ba^{2+}$, $Ra^{2+}$, $Zn^{2+}$, $Cd^{2+}$, $Hg^{2+}$, $Tl^{30}$, $Pb^{2+}$, (lanthanide)$^{3+}$. |

Whenever a cation is present, an anion is also present in the PACmn.M complex. The anion moiety of the compounds which form the cation source(s) typically are selected from this group: $F^-$, $Cl^-$, $Br^-$, $I^-$, $At^-$, $BF_4^-$, $PF_6^-$, $BPh_4^-$, $CF_3SO_3^-$, $SCN^-$, $NO_3^-$, picrate$^-$, $SiF_6^{2-}$, $SO_4^{2-}$, $PO_4^{3-}$. Noncoordinating anions such as $PF_6^-$, $BF_4^-$, and $BPh_4^-$ are preferred. Care must be taken to avoid combinations of cations and anions that have a large crystal lattice free energy since this may prevent complexation by the crown ether. Examples of inappropriate combinations are AgCl and $BaSO_4$. The importance of the crystal lattice free energy of the salt is discussed by Liotta in "Synthetic Multidentate Macrocyclic Compounds", pages 114 and 115.

The process for preparing $PACmn.M_{0,1}$ will vary somewhat depending upon whether m is 0 or an integer from 1 to 4. When m is 0, the process typically comprises reacting the appropriate diaryl phosphine chloride and aza-containing crown ether in the presence of triethylamine and an ether solvent. When a complex with a cation is being prepared, an appropriate source of cation(s) is added to the reaction mixture. In this manner, compounds of the formula $PAC0n.M_{0,1}$ are made.

When m is 1, the process typically comprises reacting a diaryl phosphine ($Ar_2PH$), an aza-containing crown ether, and aqueous formaldehyde in the presence of a solvent such as toluene, benzene or the like. When m is 2 to 4, the process typically comprises reacting an appropriate chloroalkyl-substituted diaryl phosphine and aza-containing crown ether in the presence of a base such as $Na_2CO_3$ or the like.

This invention also concerns adducts of the $PACmn.M_{0,1}$ compounds of this invention with hydroformylation catalyst precursors. It is also an aspect of this invention that rate enhancements are generally obtained with $PACmn.M_1$ over $PACmn.M_0$ complexes. Preferred adducts are those with Rh— and Co— containing hydroformylation catalyst precursors. Adducts comprising Rh have the general formula Rh XL $(PACmn.M_{0,1})_S$ wherein:
X=H, Cl, Br, or I,
L=1,5-cyclooctadiene, norbornadiene or CO,
when, X=H and L=CO, then S=3,
when X=Cl, Br or I and L=CO, then S=2,
when X=Cl, Br or I and L=1,5-cyclooctadiene or norbornadiene, then S=1.

Adducts comprising Co have the general formula:

$Co_2(CO)_6(PACmn.M_{0,1})_2$ or $HCo(CO)_3(PACmn.M_{0,1})$.

The most preferred Rh— containing adduct is

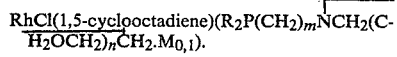

The most preferred Co— containing adduct is

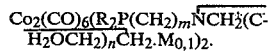

Hydroformylation reactions employing the described ethers, ether complexes, and/or adducts are also included within the scope of this invention. Representative of the hydroformylation reactions contemplated within the scope of this invention is the hydroformylation of propene to $C_4$ aldehydes which proceeds as follows:

$CH_3CH=CH_2 + CO + H_2 \xrightarrow{catalyst}$ (1)

$CH_3CH_2CH_2CHO + (CH_3)_2CHCHO$.

The process of this invention comprises operating (1) in the presence of an adduct of this invention as catalyst. The reaction can be carried out over a temperature range of about 80° to 180° C. and pressures of about 500 to 4000 psi. Enhanced reaction rates are observed when the $PACmn.M_{0,1}$ complexes are employed with Rh and Co catalyst precursors as described herein. For additional background information on reaction (1), see Pruett, Advances in Organometallic Chemistry, 17 (1971), pages 1 to 60.

DETAILS OF THE INVENTION

Typical reaction sequences illustrating processes for making the ethers and ether complexes of this invention are as follows:

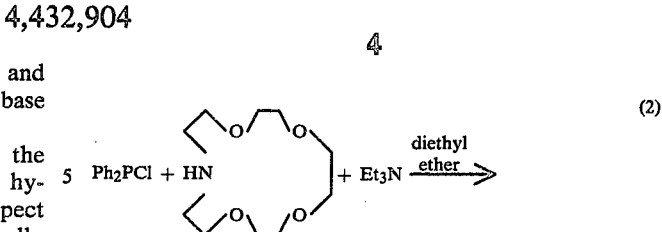

(2)

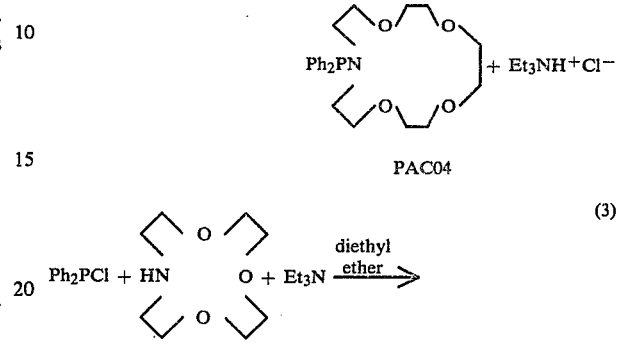

(3)

PAC03

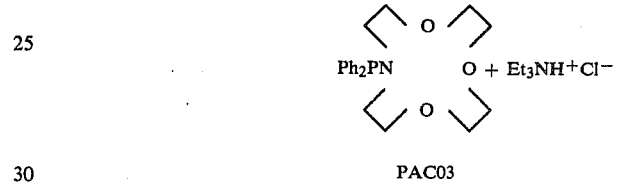

(4)

PAC14

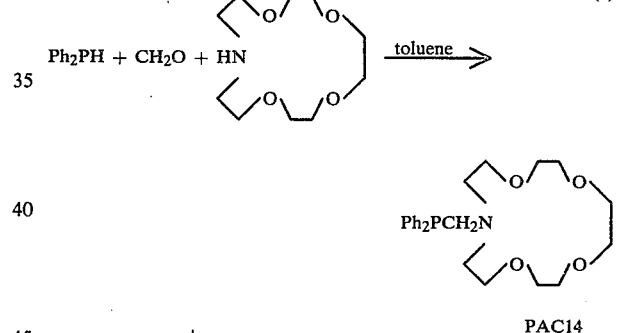

(5)

PAC24

The triethylamine employed in reactions (2) and (3) is not necessary to the reaction. However, in the absence thereof the yield will be only about 50% versus approximately a quantitative yield when the triethylamine is present. The reactants are used in approximately 1:1 or 1:1:1 stoichiometry depending on the reactants and the products being made. There appears to be no advantage to using any of these reactants in excess.

The cation-containing compounds PACmn.M₁ are made by combining PACmn.M₀ compounds with the appropriate cation-containing salt in a polar solvent such as methylene chloride (preferred). Other solvents that can be used include THF, chlorinated aromatic compounds, alcohols such as methanol and ethanol, and the like. Tertiary amine bases may be used in reactions (2) and (3). However, Et₃N is preferred because it is volatile and can be removed easily by vacuum after its use.

The following Examples illustrate this invention.

EXAMPLE 1
PAC03

Monoaza-12-crown-4 (0.422 g, 2.41 mmol) and Et₃N (0.293 g, 2.89 mmol) were dissolved in 20 ml of ether. A solution of Ph₂PCl (0.531 g, 2.41 mmol) in 5 ml of ether was added dropwise over a period of 5 min. A white flocculent precipitate of Et₃NH⁺Cl⁻ formed immediately. After stirring for 30 min, the mixture was filtered and the filtrate was evaporated to an oil. The oil was extracted into pentane, filtered, and evaporated to give 0.861 g (99%) of a colorless oil. ¹H NMR (C₆D₆, 80 MHz): 3.34 (m, OCH₂CH₂O, NCH₂C$\underline{H}$₂O); 3.45 (t, J=4.0 Hz, NC$\underline{H}$₂CH₂O); 7.15, 7.58 (m, m, Ph).

EXAMPLE 2
PAC03.LiPF₆

PAC03 (0.516 g, 1.44 mmol) and LiPF₆ (0.262 g, 1.72 mmol) were combined in 15 ml of CH₂Cl₂ and stirred for 90 min. The solution was filtered to remove excess LiPF₆, and evaporated to a white crystalline solid (0.728 g) (99%).

EXAMPLE 3
PAC04

In a procedure similar to that of Example 1, 5.00 g (22.8 mmol) of monoaza-15-crown 5, 5.03 g (22.8 mmol) of PPh₂Cl and 2.77 g (27.36 mmol) of Et₃N were dissolved in 200 ml of dry ether. The product, a colorless oil, weighed 9.01 g (98%). ¹H NMR (C₆D₆, 360 MHz): 3.33 (s, OCH₂CH₂O); 3.38 (s, OCH₂CH₂O); 3.40 (dt, J$_{HH}$=6.5 Hz, J$_{PH}$=10.0 Hz, NC$\underline{H}$₂CH₂O); 3.55 (t, J=6.3 Hz, NCH₂C$\underline{H}$₂O); 7.12 (m, Ph); 7.54 (m, Ph). ¹³C [¹H] NMR (C₆D₆, 100.6 MHz): 25.85 (d, J$_{CP}$=14.1 Hz, N$\underline{C}$H₂CH₂O); 42.85, 43.19, 44.10, 44.30 (s, s, s, s, NCH₂$\underline{C}$H₂O and OCH₂CH₂O); 100.84 (d, J$_{CP}$=4.3 Hz, m—$\underline{C}$₆H₅); 100.86 (s, p—$\underline{C}$₆H₅); 104.89 (d, J$_{CP}$=19.9 Hz, o—$\underline{C}$₆H₅); 113.05 (d, J$_{CP}$=16.3 Hz, i—$\underline{C}$₆H₅). Mass spectrum (electron impact): 403.1929 (molecular ion calc. 403.1913); 214.0779 (base peak, Ph₂PNH(CH₂)⁺).

EXAMPLE 4
PAC04.NaPF₆

PAC04 (0.771 g, 1.91 mmol) and NaPF₆ (0.385 g, 2.29 mmol) were combined in about 10 ml of CH₂Cl₂ and stirred for 12 hours. The white solid product was obtained in quantitative yield.

EXAMPLE 5
PAC14

Monoaza-15-crown-5 (11.30 g, 51.5 mmol), aqueous formaldehyde (5.53 g of 37% solution, 68.1 mmol), and Ph₂PH (9.60 g, 51.5 mmol) were combined in 40 ml of benzene and heated to 60° C. for 5 hr under argon. The mixture was evaporated to a yellow oil under high vacuum, and dehydrated by refluxing in a Dean-Stark trap with 120 ml of benzene for 3 hr. The benzene solution was evaporated to an oil and the product was extracted into pentane, filtered, and evaporated to a pale yellow oil, 20.98 g (98%).

¹H NMR (CDCl₃ 80 MHz): 2.97 (t, 4, J=6 Hz, NCH₂C$\underline{H}$₂O); 3.47 (d, J$_{PH}$=4.4 Hz, PCH₂N); 3.63 (s, t, J=6 Hz, OCH₂CH₂O and NCH₂C$\underline{H}$₂O); 7.4 (m, 10, C₆H₅). IR showed absence of an OH band. ³¹P [¹H] NMR (C₆D₆, 32.20 MHz): −26.4. ¹³C [¹H] NMR (C₆D₆, 22.63 MHz): 56.3 (d, J$_{CP}$=7.4 Hz, PCH₂N); 60.9 (d, J$_{CP}$=2.9 Hz, N$\underline{C}$H₂CH₂O); 70.3, 70.5, 70.9, 71.5 (s, s, s, s, NCH₂$\underline{C}$H₂O and OCH₂CH₂O); 128.6 (d, J$_{CP}$=7 Hz, p—$\underline{C}$₆H₅); 128.5 (s, m—$\underline{C}$₆H₅); 133.4 (d, J$_{PC}$=18 Hz, o—$\underline{C}$₆H₅); 139.4 (d, J$_{PC}$=15 Hz, i—$\underline{C}$₆H₅). Mass spectrum (electron impact): 232.1551 (base peak, CH₂=$\overline{\text{N}}$CH₂(CH₂OCH₂)₄CH₂).

EXAMPLE 6
PAC14.NaPF₆

PAC14 (3.008 g, 7.21 mmol) was dissolved in 40 ml of CH₂Cl₂, and NaPF₆ (1.33 g, 7.93 mmol) was added while stirring. Initially, the portions of NaPF₆ dissolved, but by the end of the addition there was undissolved white solid. The mixture was stirred overnight, filtered, and evaporated to give a sticky white solid slightly soluble in ether, moderately soluble in toluene, and very soluble in CH₂Cl₂ and THF. The product was extracted with 2×12 ml ether, and filtered to yield a dry white solid 3.95 g (94%). Recrystallization from about 200 ml of toluene/CH₂Cl₂ (9:1) at −78° C. gave 3.23 g of white solid (two crops, 76%).

¹H NMR (CDCl₃, 90 MHz):2.91 (t, 3, J=5 Hz, NC$\underline{H}$₂CH₂O); 3.40 (t, 3, J=5 Hz, NCH₂C$\underline{H}$₂O); 3.60, 3.65 (s, s, 12, OCH₂CH₂O); 3.92 (s, 2 NCH₂P); 7.33 (m, 10, C₆H₅). ¹H NMR indicated that the crystals contained variable amounts of toluene removable very slowly by high vacuum drying at 25° C. IR showed the absence of an OH band.

EXAMPLE 7
PAC24

A mixture of Ph₂PCH₂CH₂Cl (0.25 g, 1.0 mmol), monoaza-15-crown-5 (0.22 g, 1.0 mmol), and sodium carbonate (0.16 g, 1.5 mmol) was heated to 120° C. in an evacuated, sealed flask for 15 hr. The mixture was extracted with hexane, and the extracts were evaporated to a pale yellow oil (0.35 g).

¹H NMR showed: PAC24 (66%), Ph₂PCH=CH₂ (16%), and monoaza-15-crown-5 (12%). ¹H NMR of PAC24 (C₆D₆, 360 MHz): 2.242 (m, PC$\underline{H}$₂CH₂N); 2.743 (t, J=6.1 Hz, NC$\underline{H}$₂CH₂O); 3.385 (s, OCH₂CH₂O); 3.469 (m, PCH₂C$\underline{H}$₂N); 3.491 (s, OCH₂CH₂O); 3.573 (t, J=6.1 Hz, NCH₂C$\underline{H}$₂O); 7.06, 7.44 (m, m, Ph).

EXAMPLES 8 TO 17

The general procedure employed in the Examples and control experiments of Table 1 is summarized hereafter. In each of the Examples, a PAC compound or an alkali metal adduct thereof was employed as a promoter for the Rh-compound-catalyzed hydroformylation reaction. The "initial turnover rate" measurements given in the Table are useful to show rate enhancement, i.e., effectiveness of the compounds of this invention in promoting catalytic hydroformylation reactions.

Propene was selected as the olefin reactant for this study of hydroformylation. Propene was selected because it is an important industrial hydroformylation reactant and results achieved with it indicate the results to be expected with other typical α-olefinic reactants. The hydroformylation of propene proceeds as follows:

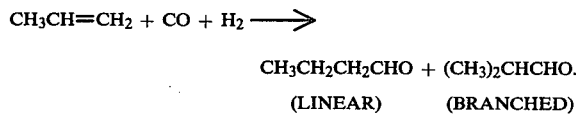

$$CH_3CH=CH_2 + CO + H_2 \longrightarrow$$
$$CH_3CH_2CH_2CHO + (CH_3)_2CHCHO.$$
$$\text{(LINEAR)} \quad \text{(BRANCHED)}$$

PROCEDURE

A 330 or 400 ml shaker tube (stainless steel) is flushed with $N_2$, charged with a methylene chloride solution of the rhodium compound and a methylene chloride solution of the phosphine azacrown ether (or alkali metal adduct). The vessel is chilled with dry ice, evacuated, and the olefin (propene) is condensed into the tube. After being charged, the tube is sealed and connected to a pressure cell and heated to reaction temperature. A gas mixture of $3CO/2H_2$ is introduced into the tube until the desired pressure is reached. During the reaction time of one hour, the tube is not repressurized, but a pressure/time curve is recorded for the reaction. After the tube is cooled to room temperature, the liquid discharge is analyzed by means of standard gas chromatographic procedures.

The pressure/time curve gives initial reaction rates at low conversion. The initial rate is normalized for the moles of initially charged rhodium. The units for the defined normalized initial rate are mol aldehyde/mol Rh/hr. All the experiments were performed at 6.9 MPa (1000 psi) and 120° C.

Experimental results are summarized in Table 1 and depicted as ratios of reaction rates in Table 2. Table 2 shows that there is a rate enhancement for the alkali metal phosphine azacrown ethers when compared to the parent azacrown ethers. However, in the presence of a cryptand that binds the cation the catalytic activity is approximately that of the paarent azacrown ether without the cation; see Examples 14 and 17, Table 1.

The rhodium dimer, $[Rh(COD)Cl]_2$, used in this study can be replaced by chlorodicarbonylrhodium dimer, chloronorbornadiene rhodium dimer, chlorobis(ethylene)rhodium dimer or other dimers which are cleaved in the presence of phosphines to give $LRhCl(PACmn.M_{0,1})$ where L is norbornadiene, and $LRhCl(PACmn.M_{0,1})_2$ where L is ethylene or CO. It is also expected that the adduct, $HRh(CO)[PACmn.M_{0,1}]_3$, can be preformed starting with the above dimers by chemistry analogous to that developed for $HRh(CO) (\phi_3P)_3$. See Cotton et al., Advanced Inorganic Chemistry, 4th Edition, John Wiley and Sons, 1980, page 937.

Similar cobalt hydroformylation catalyst adducts are also expected to be preparable using the phosphine azacrown ethers. For example:

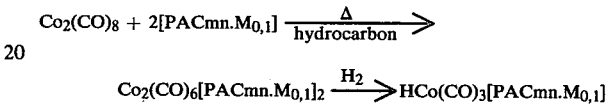

$$Co_2(CO)_8 + 2[PACmn.M_{0,1}] \xrightarrow[\text{hydrocarbon}]{\Delta}$$

$$Co_2(CO)_6[PACmn.M_{0,1}]_2 \xrightarrow{H_2} HCo(CO)_3[PACmn.M_{0,1}]$$

Such an approach would operate for both Rh and Co compounds to be combined with phosphine azacrown ethers and alkali metal adducts thereof.

The following explanations apply to terms employed in Table 1:
$[Rh(COD)Cl]_2 = 0.101$ mmol or '$Rh(COD)Cl$' $= 0.202$ mmol
COD = 1,5-cyclooctadiene
Solvent: 30.0 ml methylene chloride
CRYPTAND =

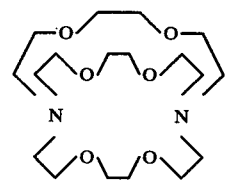

Yield = mols aldehyde/mols olefin present initially
Init. Turnover Rate = mol of aldehyde/mol of Rh/hr.

TABLE 1

Hydroformylations Promoted by Phosphine Azacrown Ether Ligands

| Example or Control | Ligand (mmol) | [Rh(COD)Cl]$_2$ (mmol) | % Yield | Init. Turnover Rate × 10$^{-3}$ | |
|---|---|---|---|---|---|
| Control | None Et$_3$N (0.40) | (0.101) | 40.4 | 2.32 | } avg. 2.41 |
| Control | None Et$_3$N (0.40) | (0.101) | 42.0 | 2.50 | |
| Example 8 | PACO3 (0.44) | (0.101) | 33.8 | 2.99 | |
| Example 9 | PACO3 (0.44) + NaPF$_6$ (1.0) | (0.101) | 36.2 | 7.62 | |
| Example 10 | PACO3 (0.44) + LiPF$_6$ (0.44) | (0.101) | 33.4 | 4.82 | |
| Example 11 | PACO4 (0.44) | (0.101) | 36.8 | 6.14 | } avg. 5.99 |
| Example 12 | PACO4 (0.44) | (0.101) | 38.8 | 5.84 | |
| Example 13 | PACO4 (0.44) | (0.101) | 31.0 | 7.49 | |

TABLE 1-continued
Hydroformylations Promoted by Phosphine Azacrown Ether Ligands

| Example or Control | Ligand (mmol) | [Rh(COD)Cl]$_2$ (mmol) | % Yield | Init. Turnover Rate × 10$^{-3}$ |
|---|---|---|---|---|
| | + NaPF$_6$ (0.44) | | | |
| Example 14 | PACl4 (0.101) | | 20.7 | 1.32[1] |
| Example 15 | PACl4 (0.44) + NaPF$_6$ (0.44) | (0.101) | 42.0 | 6.94 |
| Example 16 | PACl4 (0.44) + NaPF$_6$ (0.44) | (0.101) | 35.8 | 6.15 |
| Example 17 | PACl4 (0.44) + NaPF$_6$ (0.44) + CRYPTAND (0.48) | (0.101) | 14.9 | 1.29[2] | avg. 6.55 (for Examples 15 and 16)

[1]This initial turnover rate is somewhat low because the —CH$_2$— group between the P and the N in the azacrown ether is believed to act as an insulating group effecting a more basic phosphine than for azacrown ether in which there are no —CH$_2$— groups between the P and the N heteroatoms.
[2]This value is approximately the same as that of Example 14 because the cryptand removes the cation from the PAC complex undermining said cation's ability to enhance the turnover rate.

TABLE 2
Enhancement Ratios For Cation-Containing PAC's Versus PAC's Containing No Cations, Summarized From Table 1

| LIGAND | Init. Turnover Rates From Table 1 | Init. Turnover Enhancement (Ratio) |
|---|---|---|
| PACO3.Na$^+$/PACO3 | 7.62/2.99 | 2.55 |
| PACO3.Li$^+$/PACO3 | 4.82/2.99 | 1.61 |
| PACO4.Na$^+$/PACO4 | 7.49/5.99 | 1.25 |
| PACl4.Na$^+$/PACl4 | 6.55/1.32 | 4.96 |

The embodiments of the invention in which an exclusive property or privilege is claimed are defined as follows:

1. A phosphine azacrown compound having the formula:

R$_2$P(CH$_2$)$_m$NCH$_2$(CH$_2$OCH$_2$)$_n$CH$_2$·M$_{0,1}$ wherein
R is selected from the group consisting essentially of phenyl, naphthyl, substituted phenyl, and substituted naphthyl, the substituents being selected from the group consisting essentially of hydrocarbyl of up to about 6 carbons, alkoxy of 1 to 4 carbons, halogen, and CF$_3$;
m is 0 to 4;
n is 3 to 6; and
M is a cation selected from the group consisting essentially of Li$^+$, Na$^+$, K$^+$, Rb$^+$, Tl$^+$, Cs$^+$, Fr$^+$, Ca$^{2+}$, Zn$^{2+}$, Cd$^{2+}$, Hg$^{2+}$, Sr$^{2+}$, Ba$^{2+}$, Ra$^{2+}$, Pb$^{2+}$, and lanthanide$^{3+}$; when a cation is present, the corresponding anion is selected from the group consisting essentially of F$^-$, Cl$^-$, Br$^-$, I$^-$, At$^-$, BF$_4^-$, PF$_6^-$, BPh$_4^-$, CF$_3$SO$_3^-$, SCN$^-$, NO$_3^-$, picrate$^-$, SiF$_6^{2-}$, SO$_4^{2-}$, and PO$_4^{3-}$.

2. A compound according to claim 1 wherein R is phenyl.

3. A compound according to claim 2 wherein m is 0 or 1 and n is 3 or 4.

4. A compound according to claim 3 wherein m is 0 and n is 3.

5. A compound according to claim 3 wherein m is 0, n is 3, and M is Li$^+$ or Na$^+$.

6. A compound according to claim 3 wherein m is 0 and n is 4.

7. A compound according to claim 3 wherein m is 0, n is 4, and M is Li$^+$ or Na$^+$.

8. A compound according to claim 3 wherein m is 1 and n is 4.

9. A compound according to claim 3 wherein m is 1, n is 4, and M is Li$^+$ or Na$^+$.

10. A compound according to claim 2 wherein m is 2 and n is 4.

* * * * *

UNITED STATES PATENT AND TRADEMARK OFFICE
CERTIFICATE OF CORRECTION

PATENT NO. : 4,432,904

DATED : February 21, 1984

INVENTOR(S) : Stephan James McLain and Francis Joseph Waller

It is certified that error appears in the above—identified patent and that said Letters Patent is hereby corrected as shown below:

Column 2, second column of the Table in the penultimate line, "Tl30" should read --$Tl^{3+}$--.

Columns 8 and 9, TABLE 1, in the column headed "Init. Turnover Rate x $10^{-3}$":

(i) the brace pointing to "avg. 2.41" should encompass the numerals "2.32" and "2.50" and should not include the numeral "2.99".

(ii) the brace pointing to "avg. 5.99" should encompass the numerals "6.15" and "5.84" and should not include the numeral "7.49".

(iii) the brace pointing to "avg. 6.55" should encompass the numerals "6.94" and "6.15" and should not include the numeral "1.29".

Claim 1, column 9, line 47, the formula should read:

$$R_2P(CH_2)_m\overline{NCH_2(CH_2OCH_2)_n}CH_2 \cdot M_{0,1}.$$

Signed and Sealed this

Twentieth Day of November 1984

[SEAL]

Attest:

Attesting Officer

GERALD J. MOSSINGHOFF

Commissioner of Patents and Trademarks